United States Patent [19]
Kohn et al.

[11] Patent Number: 6,057,346
[45] Date of Patent: May 2, 2000

[54] INHIBITION OF RETROVIRAL LTR PROMOTERS BY CALCIUM RESPONSE MODIFIERS

[75] Inventors: Elise C. Kohn, Olney; Lance A. Liotta, Potomac; Kevin L. Gardner, Gaithersburg, all of Md.

[73] Assignee: The United States of America as represented by the Department of Health and Human Services, Washington, D.C.

[21] Appl. No.: 08/353,765

[22] Filed: Dec. 12, 1994

[51] Int. Cl.[7] .......................... A61K 31/41; A01N 43/64
[52] U.S. Cl. .................... 514/359; 514/383; 514/398; 514/407; 514/396; 514/399; 514/255; 514/256; 514/258; 514/261
[58] Field of Search ..................... 514/359, 385, 514/383, 398, 407, 396, 399, 255, 256, 258, 261

[56] References Cited

U.S. PATENT DOCUMENTS

| | | | |
|---|---|---|---|
| 4,000,197 | 12/1976 | Barfknecht et al. | 260/570.8 |
| 4,289,787 | 9/1981 | Molloy et al. | 424/329 |
| 5,132,315 | 7/1992 | Kohn et al. | |
| 5,359,078 | 10/1994 | Kohn et al. | |

FOREIGN PATENT DOCUMENTS

| | | |
|---|---|---|
| 1231690 | 12/1967 | Germany. |
| 2541184 | 4/1976 | Germany. |
| 9511221 | 4/1995 | WIPO. |
| 9518134 | 7/1995 | WIPO. |
| 9521815 | 8/1995 | WIPO. |

OTHER PUBLICATIONS

Horluism et al, 1991, Jap Infects Diseases vol. 164 pp. 53–60.
Aaronson, *Science* 254:1146–1153 (1991).
Berridge, et al., *Nature* 341:197–205 (1989).
Chapron, et al., *Biochem. Biophs. Res. Comm.* 158:527–533 (1989).
Chuvpilo et al. (1993) *Nuc. Acids Res.* 21(24): 5694–5704.
Clark, et al., *Cell.* 65:1043–1051 (1991).
Cole et al., *Cancer Metastasis Rev.* 13(1): 31–44 (1994).
Felder, et al., *J. Pharm. Exp. Therapeut.* 257:967–971 (1991).
Gusovsky, et al., *J. Biol. Chem.* 268:7768–7772 (1993).
Hupe, et al., *J. Biol. Chem.* 266:10136–10142 (1991).
Kohn, et al., *J. Natl. Cancer Inst.* 82:54–60 (1990).
Kohn, et al., *Cancer Res.* 52:3208–3212 (1992).
Lowenthal (1988) *Proc. Natl. Acad. Sci. USA* 85: 4468–4472.
Masuda et al. (1993) *Molecular and Cellular Biology* 13(12): 7399–7407.
Merritt, et al., *J. Biol. Chem* 271:515–522 (1990).
Shaw, et al. (1988), *Science* 241: 202–205.
Siekevitz et al., *Science* (1987) 238 (4833): 1575–1578.
Tanaguchi, et al., *J. Biol. Chem.* 268:2277–2279 (1993).
Arjona et al., "Sterochemistry of the reduction of the imino group. IV. Stereochemistry of the reduction of N–(1–phenylethyl)–1–alkyl–1–arylmethanimines," *An. Quim. Ser. C* 81(1):23–29 (1985).
Freifelder, "Selective Hydrogenolysis. Dehalogenation in the Presence of N–Benzyl Linkage," *J. Org. Chem.* 31(11):3875–3877 (1966).
Grethe et al., "Syntheses in the Isoquinoline Series. Synthesis of 2,3–Dihydro–4(1H)–isoquinolones," *J. Org. Chem.* 33(2):491–494 (1968).
Hiroi et al., "A Highly Efficient and Recyclable Chiral Director for Asymmetric Synthesis of Sulfoxides," *Chemistry Letters* pp. 1595–1598 (1980).
Hiroi et al., "Studies on Chiral Organo–Sulfur Compounds. I. Asymmetric Synthesis of Sulfoxides with Optically Active o–Aminoalkylphenol Derivatives," *Chem. Pharm. Bull.* 31:3471–3485 (1983).
Kametani et al., "Studies on the Synthesis of Heterocyclic Compounds. Part 687. Asymmetric Synthesis of Salsolidine," *J. Chem. Soc. Perkin Trans. 1* pp. 579–581 (1977).
Kang et al., "Rhodium(I)–catalysed Asymmetric Hydrogenation of Imines," *J. Chem. Soc. Chem. Commun.* pp. 1466–1467 (1988).
Kienzle et al., "1,5–Dihydroimidazoquinazolinones as blood platelet aggregation inhibitors," *Eur. J. Med. Chem.—Chem. Ther.* 17:547–556 (1982).
Kozlov et al., "Reductive animation of 1–acetylcyclohexene by nitriles," *Vestsi Akad. Navuk BSSR, Ser. Khim. Navuk* pp. 55–58 (1977.
Mori et al., "Formic Acid Reduction. XI. Reduction of Schiff Bases," *Chem. Pharm. Bull.* 19:1722–1727 (1971).
Standridge et al., "Phenylalkylamines with Potential Psychotherapeutic Utility. 1. 2–Amino–1–(2, 5–dimethoxy–4–methylphenyl) butane," *J. Med. Chem.* 19:1400–1404 (1976).
Standridge et al., "Phenylalkylamines with Potential Psychotherapeutic Utility. 2. Nuclear Substituted 2–Amino–1–phenylbutanes," *J. Med. Chem.* 22:154–162 (1980).
Hashimoto et al., "Highly Diastereoselective Addition of Organometallic Reagents to Chiral Almines Derived from 1–(2–Methoxyphenyl) ethylamine," *Synlett* 9:961–962 (1995).

(List continued on next page.)

*Primary Examiner*—James H. Reamer
*Attorney, Agent, or Firm*—Townsend and Townsend and Crew

[57] ABSTRACT

A class of calcium-response modification compounds is disclosed which inhibits the activation of retroviral LTR promoters, including the HIV-LTR. This class of compounds are used to delay or suppress the transition of a retroviral infection from a latent to a virulent condition, thereby ameliorating retrovirally caused diseases such as AIDS. The compounds are also useful in cancer treatment, allowing for coordinated therapeutic approaches to retroviral diseases and related cancers such as AIDS and Kaposi's Sarcoma. The compounds are also useful in standardizing in vitro assays of clinical and experimental importance.

21 Claims, 1 Drawing Sheet

OTHER PUBLICATIONS

Majewski and MacKinnon, "Enantioselective deprotonation of protected 4–hydroxycyclohexanones," *Can. J. Chem.* 72(7):1699–1704 (1994).

Wang and Backvall, "Ruthenium–catalysed Transfer Hydrogenation of Imines by Propan–2–ol," *J. Chem. Soc., Chem. Commun.* pp. 980–982 (1992).

```
                        SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 23 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:1:

CCGCTGGGGA CTTTCCAGGG AGG                                          23
```

INHIBITION OF RETROVIRAL LTR PROMOTERS BY CALCIUM RESPONSE MODIFIERS

BACKGROUND OF THE INVENTION

Infection by human immunodeficiency virus (HIV) in vivo often involves a long latency period before the development of an acute virally-mediated disease (e.g., AIDS). The events that trigger a transition from latent viral infection to full-blown AIDS are not completely understood (See, e.g., Paul (ad) *Fundamental Immunology* Third Edition, Raven Press Ltd., New York (1993) Chapter 39 for an overview of HIV infection and AIDS). However, the activation of the HIV-LTR promoter is dependent upon factors that are normally involved in regulating lymphokine production necessary for T cell activation. In many respects, HIV-1 LTR regulation is similar to, for example, the regulation of IL-2 (see Siekevitz et al., *Science* (1987) 238 (4833): 1575–1578; Shaw, et al. (1988), *Science* 241: 202–205; Masuda et al. (1993) *Molecular and Cellular Biology* 13(12): 7399–7407; Chuvpilo et al. (1993) *Nuc. Acids Res.* 21(24): 5694–5704, and Lowenthal (1988) *Proc. Natl. Acad. Sci. U.S.A.* 85:4468–4472).

It is the similarity between HIV-LTR activation and T cell activation that is thought to account for the seemingly paradoxical effect of cyclosporin A upon HIV induction. Cyclosporin A is a known T cell suppressive agent, so it would not appear to be a likely candidate as an AIDS therapeutic, since AIDS also results in T cell suppression. However, the similarity between T cell activation mechanisms and HIV-activation mechanisms actually suggested that cyclosporin A would act to inhibit the HIV LTR, since it was known to inhibit T cell activation.

Siekevitz et al. (supra) demonstrated that cyclosporin A inhibited T cell specific mitogenic lectin induction of the LTR promoter by phytohemagglutinin A (PHA). However, activation of the HIV LTR by other mitogenic agents such as the mitogenic phorbol ester phorbol 12-myristic 13-acetate (PMA) were not inhibited by cyclosporin A. Despite the apparently limited ability of cyclosporin A to inhibit the HIV LTR, the drug is now in clinical trials as a potential AIDS therapeutic agent.

PHA and PMA both affect a variety of T cell activities, as well as expression from the HIV-LTR. Each of the mitogens stimulates signal transduction pathways involved in T cell activation which are partly modulated through calcium-dependent mechanisms (see Alberts et al., *Molecular Biology of The Cell* second edition Garland Publishing, Inc New York and Paul (1989); Paul (ed) *Fundamental Immunology* Third Edition, Raven Press Ltd., New York (1993) and Cole et al., *Cancer Metastasis Rev.* 13(1): 31–44 (1994)). For instance, the action of the endogenous activator of the calcium-dependent protein kinase C, diacylglycerol, is mimicked by phorbol esters such as PMA which are known to induce expression by the LTR promoter (Siekevitz et al. supra). Diacylglycerol is produced by hydrolysis of membrane phospholipids, such as phosphatidylinositol bisphosphate. Phosphatidylinositol bisphosphate is hydrolyzed to diacylglycerol and inositol triphosphate by phospholipase C-β (PLC-β) and phospholipase C-γ (PLC-γ). These enzymes are regulated through different signal transduction pathways. PLC-β is stimulated in response to ligand binding to transmembrane receptors which associate with guanine nucleotide binding protein intermediates (Berridge, et al., *Nature* 341:197–205 (1989)).

PLC-γ is stimulated by specific tyrosine phosphorylation by a receptor tyrosine kinase stimulated by ligand binding (Aaronson, *Science* 254:1146–1153 (1991)). This process is dependent upon either calcium influx or intracellular calcium mobilization (Gusovsky, et al., *J. Biol. Chem.* 268:7768–7772 (1993); Tanaguchi, et al., *J. Biol. Chem.* 268:2277–2279 (1993); and Chapron, et al., *Biochem. Biophs. Res. Comm.* 158:527–533 (1989)). The activated PLC-γ hydrolyzes membrane phosphatidyl inositol bisphosphate to yield diacylglycerol and inositol polyphosphates, which act as second messengers. Diacylglycerol may be involved in vivo with activation of HIV as suggested by phorbol ester-induction experiments, or it may be the upstream activator of other signaling molecules which operate through mobilization of calcium. PHA binds to receptor molecules, e.g., with the carbohydrate structure Gal $\beta1,4$GlcNAc$^{\beta1,6}$Man$^{\beta1,2}$GlcNAc$^{\beta1,4}$Gal (Stryer, Biochemistry Third Edition (1989) ISBN 0-7167-1843-X p. 345). PHA is also thought to activate gene expression secondary messenger systems that involve Calcium-mediated signaling events, although the details of signal transduction are not presently known (Paul, supra).

Compound 1 (carboxyamidotriazole or "CAI"), shown below, is a calcium response modifier with antiproliferative and antimetastatic activities (Kohn, et al., *J. Natl. Cancer Inst.* 82:54–60 (1990); Felder, et al., *J. Pharm. Exp. Therapeut.* 257:967–971 (1991); Kohn, et al., *Cancer Res.* 52:3208–3212 (1992) and Kohn et al U.S. Pat. No. 5,132, 315 (1992)). Compound 1 inhibits receptor-operated and voltage-gated calcium influx (Felder, et at, *J. Pharm. Exp. Therapeut.* 257:967–971 (1991); Hupe, et al., *J. Biol. Chem.* 266:10136–10142 (1991)), calcium-dependent arachidonic acid release (Felder, et al., *J. Pharm. Exp. Therapeut.* 257:967–971 (1991); Clark, et al., *Cell.* 65:1043–1051 (1991)), and tyrosine kinase phosphorylation and concomitant activation of phospholipase C-γ (Gusovsky, et al., *J. Biol. Chem.* 268:7768–7772 (1993)). The ability of CAI to inhibit selected calcium-mediated signal transduction events made it an ideal tool with which to investigate the role of calcium regulation underlying the activation of the HIV LTR promoter.

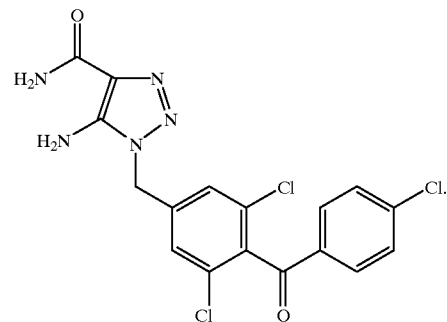

Compound 1 (CAI)

The present invention demonstrates that CAI inhibits activation of the HIV LTR promoter by the phorbol ester 12-myristic 13-acetate (PMA) and the mitogenic lectin phytohemagglutinin (PHA). Thus, the inhibition of the HIV LTR which is provided by CAI is more general than that provided by cyclosporin A, and in all likelihood represents inhibition of the signal transduction events leading to LTR activation at a different point in the regulatory cascade than cyclosporin A. This discovery provides for the use of calcium-flux modulators as AIDS therapeutics, as well as for a variety of improvements to in vitro manipulations of HIV-infected cells. These calcium-flux modulators can be compounds which are structurally related to CAI, and which are known to have similar biological properties, such as those described in co-pending application Ser. No. 08/209,089, or they can be chemically unrelated compounds that are known to have similar biological properties. For instance, Compound 2 (below) is not closely related to CAI structurally, but it is known to have comparable effects on receptor-operated calcium influx (See, Gusovsky, et al., *J. Biol. Chem.* 268:7768–7772 (1993) and Merritt, et al., *J. Biol. Chem* 271:515–522 (1990)), and can be used to inhibit the HIV-LTR.

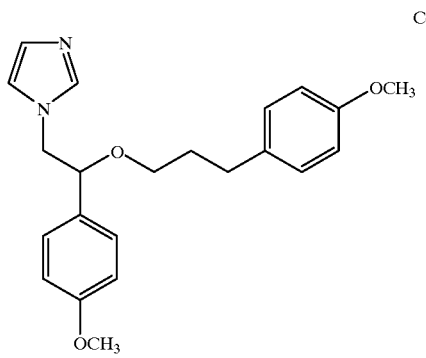

Compound 2

SUMMARY OF THE INVENTION

The HIV LTR is synergistically activated by the phorbol ester 12-myristic 13-acetate (PMA) and the T cell specific mitogenic lectin phytohemagglutinin A (PHA). This reflects the activation of the HIV LTR by endogenous T cell mechanisms in vivo. A class of calcium-response modification compounds is disclosed which is newly discovered to inhibit the activation of retroviral LTR promoters, including the HIV-LTR, by PHA and PMA. This class of compounds can be used to delay or suppress the transition of HIV infection from a latent to a virulent condition, thereby preventing or ameliorating retroviral diseases such as AIDS. The compounds are also useful in cancer treatment, allowing for coordinated therapeutic approaches to retroviral disease and related cancers such as Kaposi's Sarcoma. The compounds can also be used to standardize in vitro assays of commercial importance for clinical and experimental applications.

The present invention provides a method of modifying the response of the HIV LTR promoter in a T cell comprising treating said T cell with an effective amount of a calcium response modifier compound. An example of a T cell line in which the present invention suppresses the induction of the HIV LTR are Jurkat T cells. The calcium response modifier compound can be selected from the group of calcium response modifier compounds with the following formula:

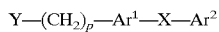

Y—$(CH_2)_p$—$Ar^1$—X—$Ar^2$ (I)

wherein:
is an integer of from 0 to 4;
$Ar^1$ and $Ar^2$ are each aromatic moieties independently selected from the group consisting of phenyl, naphthyl, and substituted versions thereof;
X is a linking moiety selected from the group consisting of O, S, $SO_2$, CO, CHCN, straight chain alkyl, alkoxy, and alkoxyalkyl; and
Y is a nitrogen-containing heterocyclic moiety selected from the group consisting of:
radicals of the formula (a)

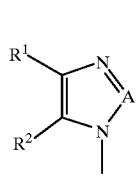

(II)

wherein:
A is N or CH,
$R^1$ is a member selected from the group consisting of hydrogen, —$CONH_2$, —$CONHR^5$, —$CO_2H$, —$CO_2R^5$, —$SO_2NH_2$,
$R^2$ is a member selected from the group consisting of hydrogen, amino, —$NHCOC_6H_5$, —$NHCOR^5$, —NHCHO, —$NHR^5$, —$N(R_5)_2$ and
$R_5$ is lower alkyl of from 1 to 6 carbon atoms, and
(b) 1,2,4-triazolyl, pyrazinyl, purinyl, pyrimidinyl, 1,2,3-triazolo-{4,5-d}-pyrimidinyl, and substituted versions thereof.

In one family of embodiments, Y is a radical of formula (II) and A is an atom such as N. $R^1$ can be a member selected from the group consisting of hydrogen, —$CONH_2$, —$CONHR^5$, and —$CO_2H$, or e.g., —$CONH_2$. For instance, in one family of embodiments, $R^1$ is —$CONH_2$, and $R^2$ is —$NH_2$. In some embodiments, p is an integer of from 0 to 2, $Ar^1$ and $Ar^2$ are substituted phenyl, X is a linking moiety selected from the group consisting of O, CO, and CHCN. In one embodiment, p is 1, $Ar^1$ is 2,6-dichlorophenyl, $Ar^2$ is 4-chlorophenyl, X is CO, Y is a radical of formula (II), A is N. $R^1$ is —$CONH_2$, and $R^2$ is —$NH_2$. In another embodiment p is 1, $Ar^1$ is 2,6-dichlorophenyl, $Ar^2$ is 4-chlorophenyl, X is CO, Y is a radical of formula (II), A is N, $R^1$ is —$CONH_2$, and $R^2$ is —NHCHO. In another embodiment p is 1, $Ar^1$ is 2,6-dichlorophenyl, $Ar^2$ is 4-chlorophenyl, X is CO, Y is a radical of formula (II), A is N, $R^1$ is —$CONH_2$, and $R^2$ is —$NHCOCH_3$. In another embodiment, p is 1, $Ar^1$ is 2,6-dichlorophenyl, $Ar^2$ is 4-chlorophenyl, X is CO, Y is a radical of formula (II), A is N, $R^1$ is —$CONH_2$, and $R^2$ is —$NHCOC_6H_5$. In another embodiment p is 1, $Ar^1$ is 2,6-dichlorophenyl, $Ar^2$ is 4-chlorophenyl, X is CO, Y is a radical of formula (II), A is N, $R^1$ is —$CO_2H$, and $R^2$ is —$NH_2$. In some embodiments, the calcium response modifier compound is carboxyamidotriazole (CAI).

The methods of the invention can be used to suppress the transition of an HIV virus from the latent to the lytic phase (i.e., from a state where the virus replicates infrequently or has low transcriptional activity to one where the virus replicates frequently and/or has high levels of transcriptional activity). This results in an alteration in the progression of AIDS in an HIV-infected patient, wherein the transition of the HIV infection to the lytic phase is suppressed, resulting in a delay or amelioration of the onset of AIDS. Because the compounds of the present invention are known to be effective in the treatment of cancer, the methods of the present invention can also comprise inhibiting the invasion and metastasis of a malignancy associated with AIDS in addition to the treatment of AIDS with the compounds of the present invention. For instance, a patient infected with an HIV virus and afflicted with cancer can be treated for both conditions by the methods of the present invention.

DETAILED DESCRIPTION

Figure 1:
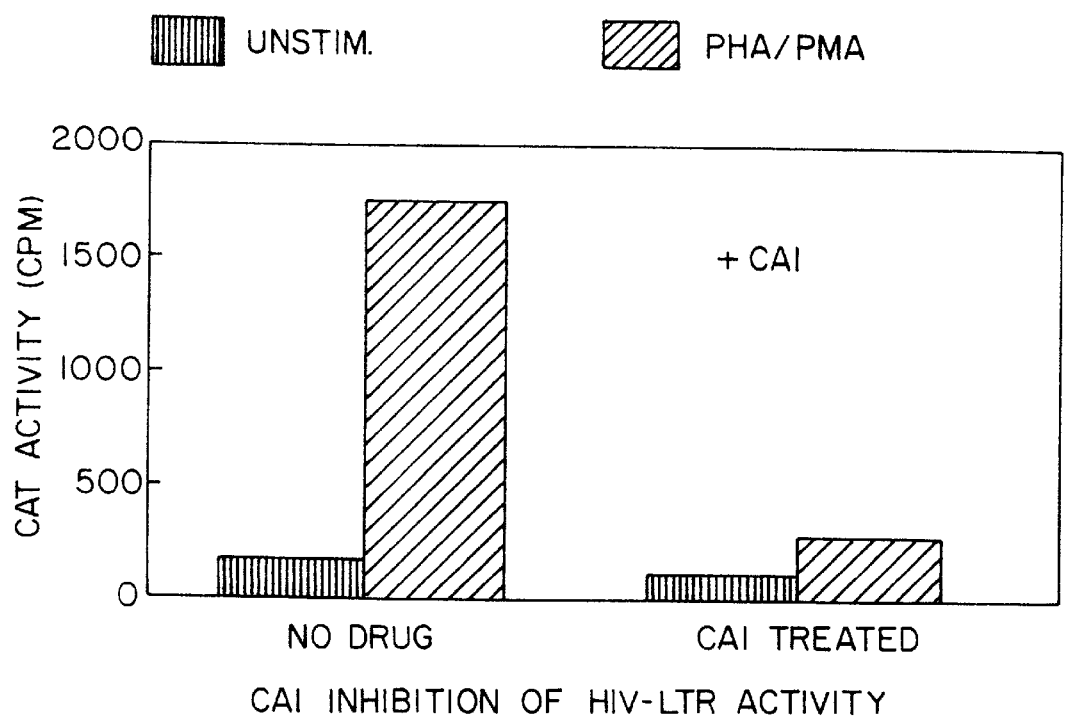
FIG. 1 is a bar graph showing the effects of CAI upon PHA/PMA mediated LTR activation.

The measurement of HIV-LTR activity in T cells in vitro is a widely accepted method for the analysis of drugs which affect T cell function and HIV activity. For instance, the anti-HIV drugs cyclosporin A and FK506 were analyzed by measuring their effects upon HIV-LTR activity in T cells. Analysis of these drugs have demonstrated the conceptual applicability of the T cell in vitro model as a predictor of in vivo human efficacy. In particular, the transformed Jurkat T cell line is widely accepted as a model system for the evaluation of signal transduction pathways that are important for T cell activation. The cells are transfected with a reporter plasmid which contains the LTR of HIV-1 linked to a reporter gene such as chloramphenicol acetyl transferase (CAT). Expression of the reporter gene is a direct reflection of the regulated activity of the HIV LTR promoter.

The activation of the HIV-LTR promoter relies upon factors that are normally involved in regulating lymphokine production during T cell activation. In order to see whether the HIV-LTR was affected by calcium-dependent signal transduction pathways, the known calcium response-modifier CAI (a carboxyamido-triazole with a halogenated benzophenone tail, depicted as compound 1 above) was tested for effect in the Jurkat T cell system described above. CAI was found to inhibit both PHA and PMA induced LTR activation, indicating that drugs which modulate calcium dependent responses have utility in modifying LTR activity.

Further supporting this utility, it was found that when T-cells are pretreated with CAI, the nuclear regulatory protein NF-κB shows reduced binding activity in T-cells. The HIV-LTR promoter contains NF-κB binding sites, and HIV-LTR expression is known to be partially dependent upon NF-κB stimulation.

A variety of calcium response modifiers are described in Kohn et al U.S. Pat. No. 5,132,315 (1992), Kohn et al., U.S. Pat. No. 5,359,078 and copending applications Ser. No. 08/209,089 and Ser. No. 08/209,651 (both filed Mar. 10, 1994) which are incorporated herein by reference. CAI and other calcium response modifiers (described below) have similar biological properties in a variety of applications, including angiogenesis inhibition, cancer therapy and inhibition of metalloproteinase expression. Calcium response modifiers with biological properties similar to CAI are effective in inhibiting LTR activation.

HIV-infected individuals often show only limited adverse effects from the infection (termed the "latent" phase) until the virus is induced to replicate at a high level (termed the "lytic" phase of infection), causing immune-system failure and associated events (e.g., AIDS) leading to death. The basic strategy for using CAI and other calcium response modifiers as anti-AIDS therapeutics is to take advantage of its LTR suppressive effects to prevent or delay the onset of AIDS and other acute HIV-induced conditions in HIV-infected individuals. This strategy can also be used to suppress the transition of other LTR-regulated retroviruses, such as the Human T cell Leukemia Virus-1 (HTLV-1), from the latent to the lytic phase, thereby ameliorating the effects of other retroviral infections.

The anti-AIDS therapeutic cyclosporin A also suppresses the transition of HIV from the latent to the lytic phase by suppressing activation of the LTR. However, as discussed above in the background to the invention, the suppression is not as effective or as general as that observed for CAI, and cyclosporin has the unwanted side effect of causing immune suppression. Since AIDS is a result of a compromised immune system, this "side effect" is difficult to balance with the drug's LTR suppressive effects.

CAI is an oral drug that is currently being used in clinical trials for patients with cancer, and has shown no severe side effects. Because CAI has superior LTR suppressive effects than known LTR modulators, and because the drug is easily administered without serious side effects, CAI is a significant anti-AIDS therapeutic. Furthermore, because calcium response modifiers are effective in the treatment and prevention of cancer (see, e.g., Kohn et al., U.S. Pat. No. 5,132,315 and copending application Ser. No. 07/985,402), AIDS patients who have developed AIDS-related cancers such as Kaposi's sarcoma will benefit from both the LTR suppressive effects of the compounds and their anti-metastatic properties.

In addition to the therapeutic uses described above for calcium response modifiers, the present invention provides commercially useful in vitro embodiments. For instance, a common problem in handling HIV-infected cells which are to be used in infectivity or viral count assays is establishing a "baseline" infectivity for the cells.

As a practical matter, one of skill will recognize that some HIV-infected cells are more easily induced to enter the lytic phase than others. As a result, some infected cells are inadvertently stimulated to undergo the lytic phase causing viral multiplication and release, with the result that any subsequent clinical or experimental assays performed on the cells yield incorrect estimates of virus counts, virulence and related phenomena. By treating cell isolates with calcium response modifiers such as CAI, the HIV virus is prevented from LTR-mediated activation. This effect is easily reversed by washing the cells to remove the calcium response modifier. The results below showing CAI suppression of the HIV LTR are reversible upon removal of CAI, e.g., by washing the cells by standard techniques.

Therefore, calcium response modifiers such as CAI are useful in maintaining HIV-infected cells in a non-lytic phase, and in providing a means for activating the cells at a specific time (e.g., after removal of the calcium response modifier). The addition of calcium response modifiers such as CAI to isolated HIV-infected cells can be used as a standard practice for the clinical and experimental manipulation of T cells.

Definitions

As used herein, the term "alkyl" refers to a saturated hydrocarbon radical which can be straight-chain or branched-chain (for example, ethyl, isopropyl, t-amyl, or 2,5-dimethylhexyl). Preferred alkyl groups are those containing 1 to 6 carbon atoms. All numerical ranges in this specification and claims are intended to be inclusive of their upper and lower limits.

The term "alkoxy" refers to an alkyl radical as described above which also bears an oxygen substituent which is capable of covalent attachment to another hydrocarbon radical (such as, for example, methoxy, ethoxy, phenoxy and t-butoxy).

The term "aromatic group" refers to a group of unsaturated cyclic hydrocarbons containing one or more rings. The rings are typified by benzene which has a 6-carbon ring containing three double bonds. Groups containing multiple rings can have the rings fused together or linked covalently. Examples of such multiple ring aromatic groups are naphthyl, biphenyl and anthracenyl. The term "aromatic group" also refers to those groups described above which contain heteroatoms, for example, pyridyl and quinoxalyl. Other aromatic groups include certain 5-membered cyclic moieties such as the furan group and the thienyl group. Any of the aromatic groups described herein can be optionally substituted with halogen atoms, or other groups such as nitro, carboxyl, alkoxy, carboxylic acids, esters, hydroxyl, amino, alkenyl, alkyl and the like.

The term "alkoxyalkyl" refers to an alkoxy radical attached directly to an alkyl group. When used as a linking group, alkoxyalkyl refers to such radicals as —$CH_2OCH_2$—, —$CH_2OCH_2CH_2$—, —$CH_2CH_2CH_2O CH_2$— and —$CH_2CH_2OCH_2CH_2$—.

The term "substituted" refers to groups having additional moieties attached, such moieties including halogen atoms, and groups such as nitro, carboxyl, alkoxy, amino, carbamoyl, carboxylic acids, esters, hydroxyl, amino, alkenyl, alkyl and the like.

The term "effective amount" of a calcium response modifier refers to an amount sufficient to suppress the activation of the LTR of interest by phorbol esters and/or phytohemagglutinins in vitro, or to suppress the activity of the LTR by endogenous T cell mechanisms such that entry of the virus into the lytic phase is suppressed in vitro or in vivo, with a concomitant reduction in viral titre, or maintenance of a low viral titre over time, as measured by standard techniques such as the polymerase chain reaction (PCR), Southern analysis, northern analysis, western analysis and ELISA assays.

The term "HIV" is used herein to refer to the human immunodeficiency virus. It is recognized that the HIV virus is an example of a hyper-mutable retrovirus, having diverged into two major subtypes (HIV-1 and HIV-2), each of which has many subtypes. However, compounds of the present invention can suppress the LTR promoters from all HIV and other retroviruses which are similar to HIV-1 in the LTR region. The present invention provides a simple CAT assay which can be used to determine whether a homologous LTR region from a retrovirus other than HIV-1 shows inhibition by calcium response modifiers. Thus, the term "HIV" used herein, unless otherwise indicated, refers to any retrovirus which is regulated by an LTR promoter or LTR promoter homologue which shows inhibition of the LTR promoter or LTR promoter homologue by calcium response modifiers.

The HIV genes coding for the viral proteins that form the core of the retroviral virion (gag), the enzymes responsible for reverse transcription (pol) and the envelope glycoproteins (env) as well as other known genes responsible for viral regulation (tat, rev, nef, vif, vpr and vpu) are contained between the long terminal repeats or "LTR" of the HIV genome which are critical for gene transcription of the viral genome. The term "LTR" is used in its broadest meaning, to refer to the structural, promoter, and enhancer elements located in the terminal regions of the RNA or transcribed DNA of a retroviral genome with the same promoter and enhancer elements as HIV-1.

Structurally Related Calcium Response Modifiers

The present invention provides a method for inhibiting LTR-directed expression, and induction of LTR expression by PHA/PMA in a T cell using calcium response modifiers. Several structurally related compounds have been demonstrated to have similar calcium response modification behavior in a variety of applications (see Kohn et al U.S. Pat. No. 5,132,315 (1992), copending application Ser. No. 07/985, 402 (filed Dec. 4, 1992) and copending applications Ser. No. 08/209,089 and Ser. No. 08/209,651 (both filed Mar. 10, 1994). In general, compounds of formula I represent a related family of calcium response modifiers with similar biological properties.

The groups $Ar^1$ and $Ar^2$ are aromatic groups. They are either the same or different. Examples of aromatic groups are phenyl, substituted phenyl, naphthyl, and substituted naphthyl.

The symbol X represents a linking group. Examples include O, S, $SO_2$, CO, CHCN, straight chain alkyl, alkoxy, and alkoxyalkyl.

The symbol Y represents a variety of structures. Some of these structures are represented by formula II:

in which A is N or CH; $R^1$ is hydrogen, —$CONH_2$ (carbamoyl), —$CONHR^5$, —$CO_2H$ (carboxyl), —$CO_2R^5$, or —$SO_2NH_2$; $R^2$ is hydrogen, —$NH_2$ (amino), —$NHCOC_6H_5$ (benzamido), —$NHCOR^5$, —NHCHO (formamido), —$NHR^5$ (alkylamino), or —$N(R^5)_2$ (dialkylamino) and $R^5$ is lower alkyl of from 1 to 6 carbon atoms. A preferred group for A is N. Preferred groups for $R^1$ are hydrogen, —$CONH_2$, —$CONHR^5$, and —$CO_2H$. Particularly preferred are —$CONH_2$ and —$CO_2H$. Preferred groups for $R^2$ are —$NH_2$, —$NHCOC_6H_5$, —$NHCOR^5$, and —$NHR^5$. Particularly preferred groups for $R^2$ are —$NH_2$ and —$NHCOR^5$.

Other structures for Y are 1,2,4-triazolyl, pyrazinyl, purinyl, pyrimidinyl, 1,2,3-triazolo-{4,5-d}-pyrimidinyl, and their substituted analogues.

The symbol p represents an integer of from 0 to 4.

In some embodiments, calcium response modifiers comprise a compound of formula I in which Y is a radical of formula II, A is N and $R^1$ is —$CONH_2$.

In other embodiments, calcium response modifiers comprise a compound of formula I in which Y is a radical of formula II, A is N, $R^1$ is —$CONH_2$, and $R^2$ is —$NH_2$.

In additional embodiments, calcium response modifiers comprise a compound of formula I in which p is an integer of from 0 to 2, $Ar^1$ and $Ar^2$ are both substituted phenyl, X is O, CO or CHCN, Y is a radical of formula II, A is N, $R^1$ is —$CONH_2$, and $R^2$ is —$NH_2$.

In the most preferred embodiment, calcium response modifiers comprise a compound of formula I in which p is 1, $Ar^1$ is 2,6-dichlorophenyl, $Ar^2$ is 4-chlorophenyl, X is CO, Y is a radical of formula II, A is N, $R^1$ is —$CONH_2$, and $R^2$ is —$NH_2$.

Making Calcium Response Modifiers

The compounds used in the present invention are either commercially available or are be prepared using conventional synthetic techniques. General synthetic routes to the novel compounds tested are provided below. Particular conditions are known to those of skill in the art. Table 1 (below) provides a representative group of structurally related compounds which have demonstrated similar biological properties.

TABLE 1

| Compound Number | A | R¹ | R² |
|---|---|---|---|
| 1 | N | carbamoyl | amino |
| 3 | N | carbamoyl | formamido |
| 4 | N | carbamoyl | acetamido |
| 5 | N | carbamoyl | benzamido |
| 6 | N | carboxyl | amino |
| 7 | CH | — | — |
| 8* | N | carbamoyl | amino |

*all Cl are replaced by H

Compound 1 can be prepared by the method described in U.S. Pat. No. 4,590,201. Briefly, 2,6-dichloro-4-methylbenzoic acid is converted to its corresponding benzoyl chloride using thionyl chloride in dimethylformamide. Reaction of this benzoyl chloride with chlorobenzene in the presence of aluminum trichloride provides 4-(4-chlorobenzoyl) 3,5-dichlorotoluene. Bromination of the methyl group is carried out using N-bromosuccinimide in the presence of catalytic amounts of dibenzoyl peroxide to provide 4-(4-chlorobenzoyl)-3,5-dichlorobenzyl bromide. The benzyl bromide is then converted to the corresponding benzyl azide using potassium azide. Treatment of the 4-(4-chlorobenzoyl)-3,5-dichlorobenzyl azide thus formed with 2-cyanoacetamide in the presence of sodium methoxide provides after workup, 5-amino-1-(4-(4-chlorobenzoyl)-3,5-dichlorobenzyl)- 1,2,3-triazole-4-carboxamide (Compound 1).

Compounds 3–5 are prepared by treating compound 1 with the appropriate anhydride (formic acetic anhydride, acetic anhydride, or benzoic anhydride).

Compound 6 can be prepared by treating compound 1 with sufficient acid to hydrolyze the carboxamide to a carboxylic acid.

Compound 7 can be prepared by the reaction of 4-(4-chlorobenzoyl)-3,5-dichlorobenzyl bromide (used in the preparation of compound 1) with imidazole in the presence of base.

Compound 8 can be synthesized beginning with 4-methylbenzophenone. Treatment of 4-methylbenzophenone with N-bromosuccinimide provides 4-bromomethylbenzophenone which is converted to its corresponding azide using sodium azide in ethanol. Treatment of the resultant azide with the anion of 2-cyanoacetamide provides compound 8.

Finally, compound 2 (shown in the Background of the Invention) can be prepared by the method described in Merritt, et al., *Biochem. J.*, 271:515–522 (1990). Briefly, 2-bromo-4'-methoxyacetophenone (Aldrich, Milwaukee, Wis., U.S.A.) is treated with imidazole to provide 1-(β-oxo-4-methoxyphenethyl)-1H-imidazole. Reduction of the ketone with sodium borohydride provides 1-(β-hydroxy-4-methoxyphenethyl)-1-H-imidazole. Alkylation of the hydroxy moiety with the p-toluenesulfonate ester of 3-(4-methoxyphenyl)-1-propanol using potassium hydroxide in dimethylsulfoxide provide Compound 2 which is isolated as its hydrochloride salt.

Administration of Calcium Response Modifiers to Patients

The compounds used in the present inventive method are administered in any suitable manner, preferably with pharmaceutically acceptable carriers. One skilled in the art will appreciate that suitable methods of administering such compounds in the context of the present invention to a patient are available, and, although more than one route can be used to administer a particular compound, a particular route can often provide a more immediate and more effective reaction than another route. It should be recognized that the administration of the compounds of the present invention are well-known for diseases other than those caused by retroviral infections, and one of skill would be able to extrapolate the information available for use of calcium response modifiers to treat these other diseases to retroviral application such as AIDS.

Pharmaceutically acceptable carriers are also well known to those who are skilled in the art. The optimal choice of carrier will be determined in part by the particular compound, as well as by the particular method used to administer the composition. Accordingly, there is a wide variety of suitable formulations of the pharmaceutical compositions of the present invention.

Formulations suitable for oral administration can consist of (a) liquid solutions, such as an effective amount of the compound dissolved in diluents, such as water, saline or PEG 400; (b) capsules, sachets or tablets, each containing a predetermined amount of the active ingredient, as solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such as carriers as are known in the art.

The active ingredient, alone or in combination with other suitable components, can be made into aerosol formulations to be administered via inhalation. These aerosol formulations can be placed into pressurized acceptable propellants, such as dichlorodifluoromethane, propane, nitrogen, and the like.

Suitable formulations for rectal administration include, for example, suppositories, which consist of the active ingredient with a suppository base. Suitable suppository bases include natural or synthetic triglycerides or paraffin hydrocarbons. In addition, it is also possible to use gelatin rectal capsules which consist of a combination of the active ingredient with a base, such as, for example, liquid triglyercides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to a patient, in the context of the present invention should be sufficient to effect a beneficial therapeutic response in the animal over time. The dose will be determined by the strength of the particular compound employed and the condition of the animal, as well as the body weight or surface area of the animal to be treated. The size of the dose also will be determined by the existence, nature, and extent of any adverse side-effects that accompany the administration of a particular compound in a particular patient. In determining the effective amount of the active ingredient to be administered in the treatment or prophylaxis of AIDS or AIDS-related cancer treatment, the physician needs to evaluate circulating plasma levels, toxicities, and tumor growth inhibition, and evidence of AIDS and/or cancer progression.

In the practice of this invention, the compounds can be administered, for example, by intravenous infusion, orally, topically, intraperitoneally, intravesically or intrathecally for treatment of AIDS, and AIDS-related cancers such as lymphomas, leukemias, and solid tumors. The preferred method of administration of calcium response modifiers will often be oral, rectal or intravenous, but the compounds can be applied in a suitable vehicle for the local and topical treatment of AIDS-related cancers.

AIDS-associated tumors such as Kaposi's sarcoma can be treated by administration of the agents taught herein (see Kohn et al., U.S. Pat. No. 5,132,315). Thus, AIDS-associated tumors are simultaneously treated in conjunction with AIDS by administration of the compounds described herein. Prevention of tumor recurrence in AIDS patients by administration of the composition in a manner intended to reach the particular site where such cells are proliferating would also be advantageous. This method can supplement treatment of AIDS or cancer by any conventional therapy including cytotoxic agents and biologic response modifiers.

For oral administration, compounds of the present invention can be administered at the rate up to 3000 mg/m$^2$ body surface area, which approximates 6 grams/day in the average patient. The compounds inhibit LTR activity at a concentration of 0.1–10 $\mu$M. Thus, the most preferred effective dose in vivo will achieve a concentration of 0.1 to 10 $\mu$M in the blood. This can be accomplished via single or divided doses. For intravenous administration, such compounds can be administered at the rate of up to about 2500 mg/m$^2$/d. For intravesicle administration, such compounds can be administered at the rate of up to about 2500 mg/m$^2$/d. For topical administration, the rate can be up to about 2500 mg/m$^2$/d. The dose for inhalation/aerosol administration can be up to about 2500 mg/m$^2$/d. Direct intraperitoneal administration can be performed using up to about 3000 mg/m$^2$/d. The dose for reservoir administration to the brain or spinal fluid can be up to about 2000 mg/m$^2$/d. For slow release intraperitoneal or subcutaneous administration, the dose can be up to about 10 g/day in a bolus. For intrathecal administration, the dose can be up to about 2000 mg/m$^2$/d.

EXAMPLES

The following examples illustrate the assays and results used to evaluate the efficacy of the compounds of this invention. The following examples are provided by way of illustration only and not by way of limitation. Those of skill will readily recognize a variety of noncritical parameters which can be changed or modified to yield essentially similar results.

Example 1

Inhibition of the HIV LTR by CAI in T Cells

Jurkat human T cells are transformed T cells derived from a lymphoma which are widely used as a system to study signal transduction events in T cells. The cells were transfected with a reporter plasmid that contained the HIV-1 LTR linked to the reporter gene chloramphenicol acetyl transferase (CAT). Expression of this construct in Jurkat cells is a direct reflection of the regulated activity of the LTR promoter. The T cell mitogens PHA and PMA are known to synergistically enhance the activation of the HIV-1 LTR (Siekvitz et al., supra). The present example demonstrates that this synergistic activation is blocked by CAI.

The chloramphenicol acetyl transferase (CAT) reporter plasmids contained either 1 copy of the complete HIV-LTR sequences upstream of the CAT gene, or 3 tandem copies of the Gibbon APE Leukemia Virus (GALV) phorbol ester response element (TRE) linked upstream of a fos minimal promoter (GALV-TRE) as a control to assess PMA activation. Jurkat human T cells were grown in RPMI 1640 media with 10% fetal calf serum to a density of 5×10$^5$. Cells were serum-starved by growth for 24 hours in RPMI media without fetal calf serum. Following serum starvation, the cells were washed with phosphate buffered saline and resuspended at a final density of 2.2×10$^7$ cells. The Jurkat cells were then transiently transfected by electroporation using standard techniques (BRL Electroporation System) with 2–10 $\mu$g of plasmid reporter DNA. Following electroporation, cells were incubated for 24–30 hours in RPMI 1640, 20% calf serum. The cells were stimulated by the addition of 2 $\mu$g/ml PHA and 100 ng/ml PMA and incubated an additional 17 hours prior to harvesting. For inhibition, cells were incubated with 10 $\mu$M CAI 5 hours prior to stimulation. Harvested cells were analyzed for CAT activity as previously described (Gorman et al. *Mol. Cell. Biol.* 2: 1044–1051 (1982)).

FIG. 1 shows the level of HIV-1 LTR activation as measured by CAT activity for unstimulated CAT reporter constructs, unstimulated CAT reporter constructs treated with CAI, PHA/PMA stimulated CAT reporter constructs and PHA/PMA stimulated CAT reporter constructs which were treated with CAI as described above. Treatment with CAI reduces the activity of the PHA/PMA induced HIV-1 LTR activity to unstimulated levels. In addition, a modest reduction in the unstimulated level of LTR activity is also observed in CAI treated cells. Similar experiments also demonstrated that the activation observed upon activation with either PHA or PMA alone was reduced to unstimulated levels by treatment with CAI.

Time and dose-response points for CAI inhibition were also determined using the CAT assay described above. CAI inhibition was measured at various concentrations of 0.5–10 $\mu$M using a 5–8 hour pre-treatment regimen. High levels of inhibition were observed at a CAI concentration of 1.0 $\mu$M for an 8-hour pre-treatment. Similar levels of inhibition were observed at a CAI concentration of 10 $\mu$M for a 5 hour pre-treatment. These effects were observed to be reversible by washing the cells free of CAI and restimulating them as described above.

Example 2

Inhibition of Nucleic Acid Binding in Activated T-Cells

To examine the effect of treatment by calcium response modifiers upon the binding of nuclear regulatory proteins to HIV-LTR promoter elements, electrophoretic mobility shift assays (EMSAs) were performed on LTR-derived oligonucleotides. The T cell mitogens PHA and PMA are known to synergistically activate the binding of NF-κB to the HIV-1 LTR. The binding of NF-κB to the HIV-LTR is necessary for the activation of the LTR promoter. The present example demonstrates that activation of NF-κB binding is blocked by CAI. This inhibitory effect was found to be fully reversible upon washing and restimulating the cells with PHA/PMA.

Jurkat T-cells were stimulated with PHA/PMA with or without CAI as described above. Nuclear extracts were generated for PHA/PMA stimulated, unstimulated, and PHA/PMA stimulated—CAI pre-treated Jurkat T-cells, essentially as described (Dignam, et al. (1983) *Methods in Enzymology* 101: 582–598). EMSAs were performed on the nuclear extracts as described (Freid and Crothers (1981) *Nuc. Acids Res.* 9: 6505–6525). The oligonucleotides used in the EMSA assays were double-stranded deoxyribose oligonucleotides derived from the HIV-1 LTR 3' NF-κB binding site (5'-CCGCTGGGGACTTTCCAGGGAGG and complement). Binding reactions were performed on 2.5–10 μg of nuclear extract for 1 hour at 24° C., with 0.2 ng (0.01 pmol) of $^{32}$P 5'-end labeled double stranded oligodeoxyribonucleotide probe in a final volume of 11–14 μl in 20 mM Hepes buffer (pH 7.5), containing 500 μg/ml Bovine serum albumin, 4 mM β-mercaptoethanol, 32–71 mM NaCl, 20% glycerol, 0.05% Tween-20 and 0.2 μg poly [d(I-C)].

The nuclear extracts derived from Jurkat T-cells which were not stimulated with PHA/PMA showed substantially lower levels of NF-κB binding than those which were derived from PHA/PMA-stimulated cells. Nuclear extracts derived from Jurkat T-cells which were treated with CAI and then stimulated with PHA/PMA had levels of NF-κB binding similar to nuclear extracts from unstimulated cells.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

What is claimed is:

1. A method of inhibiting the activity of an LTR promoter in a T cell comprising contacting said T cell containing an LTR promoter with an amount of a calcium response modifier compound effective to inhibit the activity of the LTR promoter where the calcium response modifier compound is selected from the group of calcium response modifier compounds with the formula:

$$Y-(CH_2)_p-Ar^1-X-Ar^2 \qquad (I)$$

wherein:
  p is an integer of from 0 to 4;
  $Ar^1$ and $Ar^2$ are each aromatic moieties independently selected from the group consisting of phenyl, naphthyl, and substituted versions thereof;
  X is a linking moiety selected from the group consisting of O, S, SO$_2$, CO, CHCN, straight chain alkyl, alkoxy, and alkosyalkyl;
  Y is a nitrogen-containing heterocyclic moiety selected from the group consisting of:
  radicals of the formula (II)

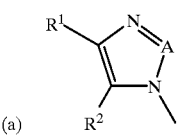

(a)

wherein:

A is N or CH;

R¹ is a member selected from the group consisting of hydrogen, —CONH₂, —CONHR⁵, —CO₂H, —CO₂R⁵, and —SO₂NH₂;

R2 is a member selected from the group consisting of hydrogen, amino, —NHCOC₆H₅, —NHCOR⁵, —NHCHO, —NHR⁵, and —N(R⁵)₂;

R⁵ is a lower alkyl of from 1 to 6 carbon atoms, and (b) 1,2,4-triazolyl, pyrazinyl, purinyl, pyrimidinyl, 1,2,3-triazolo{4,5-d}-pyrimidinyl, and substituted versions thereof.

2. The method of claim 1 wherein the LTR promoter is an HIV LTR promoter.

3. The method of claim 2, wherein Y is a radical of formula (II), and A is N.

4. The method of claim 2, wherein Y is a radical of formula (II), A is N, and R¹ is a member selected from the group consisting of hydrogen, —CONH₂, —CONHR⁵, and —CO₂H.

5. The method of claim 2, wherein Y is a radical of formula (II), A is N, and R¹ is —CONH₂.

6. The method of claim 2, wherein Y is a radical of formula (II), A is N, R¹ is —CONH₂, and R² is —NH₂.

7. The method of claim 2, wherein p is an integer of from 0 to 2, Ar¹ and Ar² are both substituted phenyl, X is a linking moiety selected from the group consisting of O, CO, and CHCN, Y is a radical of formula (II), R¹ is —CONH₂, and R² is —NH₂.

8. The method of claim 2, wherein p is 1, Ar¹ is 2,6-dichlorophenyl, Ar² is 4-chlorophenyl, X is CO, Y is a radical of formula (II), A is N, R¹ is —CONH₂, and R² is —NH₂.

9. The method of claim 2, wherein p is 1, Ar¹ is 2,6-dichlorophenyl, Ar² is 4-chlorophenyl, X is CO, Y is a radical of formula (II), A is N, R¹ is —CONH₂, and R² is —NHCHO.

10. The method of claim 2, wherein p is 1, Ar¹ is 2,6-dichlorophenyl, Ar² is 4-chlorophenyl, X is CO, Y is a radical of formula (II), A is N, R¹ is —CONH₂, and R² is —NHCOCH₃.

11. The method of claim 2, wherein p is 1, Ar¹ is 2,6-dichlorophenyl, Ar² is 4-chlorophenyl, X is CO, Y is a radical of formula (II), A is N, R¹ is —CONH₂, and R² is —NHCOC₆H₅.

12. The method of claim 2, wherein p is 1, Ar¹ is 2,6-dichlorophenyl, Ar² is 4-chlorophenyl, X is CO, Y is a radical of formula (II), A is N, R¹ is —CONH₂, and R² is —NH₂.

13. The method of claim 1, wherein said method suppresses the transition of an HIV virus from the latent to the lytic phase.

14. The method of claim 1, wherein said T cells are Jurkat T cells.

15. The method of claim 1, wherein said calcium response modifier compound is carboxyamidotriazole with the structure:

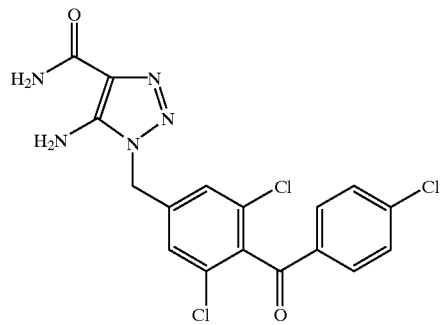

16. The method of claim 1, wherein said method further comprises inhibiting the invasion and metastasis of a malignant solid tumor.

17. The method of claim 1, wherein said method comprises inhibiting expression from the HIV LTR in vitro.

18. The method of claim 1, wherein said calcium response modifier compound is selected from the group of calcium response modifier compounds with the formula:

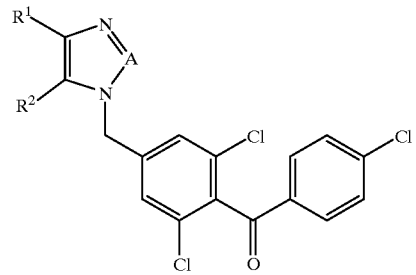

wherein A is selected from the group consisting of N and CH, R¹ is selected from the group consisting of carbamoyl, carboxyl and H, and R² is selected from the group consisting of amino, formamido, acetamido, benzamido, and H.

19. The method of claim 18, wherein A is N, R¹ is a carbamoyl, R² is an amino and wherein an H is substituted for each Cl.

20. A method of claim 1 wherein the LTR promotor is introduced into the cell by a retrovirus.

21. A method of claim 1 wherein the LTR promoter is introduced into the cell by a DNA plasmid.

* * * * *